US 9,289,011 B2

(12) United States Patent
Junker

(10) Patent No.: US 9,289,011 B2
(45) Date of Patent: Mar. 22, 2016

(54) METHOD FOR PRODUCING LUTEIN FROM TOBACCO

(71) Applicant: R.J. Reynolds Tobacco Company, Winston-Salem, NC (US)

(72) Inventor: Christopher Junker, Winston-Salem, NC (US)

(73) Assignee: R.J. Reynolds Tobacco Company, Winston-Salem, NC (US)

( * ) Notice: Subject to any disclaimer, the term of this patent is extended or adjusted under 35 U.S.C. 154(b) by 241 days.

(21) Appl. No.: 13/788,911

(22) Filed: Mar. 7, 2013

(65) Prior Publication Data
US 2014/0256829 A1    Sep. 11, 2014

(51) Int. Cl.
*A61K 36/81* (2006.01)
*A24B 15/24* (2006.01)
*C07C 403/24* (2006.01)
*A23L 1/30* (2006.01)
*A23L 1/275* (2006.01)

(52) U.S. Cl.
CPC ............ *A24B 15/241* (2013.01); *A23L 1/2751* (2013.01); *A23L 1/3002* (2013.01); *C07C 403/24* (2013.01); *C07C 2101/16* (2013.01)

(58) Field of Classification Search
USPC .................................. 424/725, 774
IPC ...................................... A61K 36/81
See application file for complete search history.

(56) References Cited

U.S. PATENT DOCUMENTS

| | | |
|---|---|---|
| 2,766,148 A | 10/1956 | Rowland |
| 2,774,680 A | 12/1956 | Hackney et al. |
| 3,424,171 A | 1/1969 | Rooker |
| 4,008,210 A | 2/1977 | Steele et al. |
| 4,009,290 A | 2/1977 | Okumori et al. |
| 4,045,879 A | 9/1977 | Witte |
| 4,056,442 A | 11/1977 | Huang et al. |
| 4,069,828 A | 1/1978 | Hall et al. |
| 4,122,104 A | 10/1978 | Witte |
| 4,144,895 A | 3/1979 | Fiore |
| 4,150,677 A | 4/1979 | Osborne, Jr. et al. |
| 4,251,671 A | 2/1981 | Alter et al. |
| 4,267,847 A | 5/1981 | Reid |
| 4,268,632 A | 5/1981 | Wildman et al. |
| 4,289,147 A | 9/1981 | Wildman et al. |
| 4,298,013 A | 11/1981 | Semp et al. |
| 4,298,540 A | 11/1981 | Youn et al. |
| 4,308,877 A | 1/1982 | Mattina |
| 4,322,569 A | 3/1982 | Chao et al. |
| 4,334,095 A | 6/1982 | Baniel |
| 4,347,324 A | 8/1982 | Wildman et al. |
| 4,351,346 A | 9/1982 | Brummer et al. |
| 4,359,059 A | 11/1982 | Brummer et al. |
| 4,359,417 A | 11/1982 | Karnofsky et al. |
| 4,381,407 A | 4/1983 | Bremus et al. |
| 4,456,556 A | 6/1984 | Grimsby |
| 4,456,557 A | 6/1984 | Grimsby |
| 4,466,923 A | 8/1984 | Friedrich |
| 4,476,881 A | 10/1984 | Gravely et al. |
| 4,506,682 A | 3/1985 | Muller |
| 4,515,726 A | 5/1985 | Sullivan |
| 4,589,428 A | 5/1986 | Keritsis |
| 4,605,016 A | 8/1986 | Soga et al. |
| 4,612,942 A | 9/1986 | Dobberstein et al. |
| 4,622,982 A | 11/1986 | Gaisch et al. |
| 4,716,911 A | 1/1988 | Poulose et al. |
| 4,727,889 A | 3/1988 | Niven, Jr. et al. |
| 4,847,106 A | 7/1989 | Pike et al. |
| 4,887,618 A | 12/1989 | Bernasek et al. |
| 4,895,175 A | 1/1990 | Baskevitch et al. |
| 4,941,484 A | 7/1990 | Clapp et al. |
| 4,967,771 A | 11/1990 | Fagg et al. |
| 4,986,286 A | 1/1991 | Roberts et al. |
| 5,005,593 A | 4/1991 | Fagg |
| 5,018,540 A | 5/1991 | Grubbs et al. |
| 5,060,669 A | 10/1991 | White et al. |
| 5,065,775 A | 11/1991 | Fagg |
| 5,074,319 A | 12/1991 | White et al. |
| 5,077,071 A | 12/1991 | Strop |
| 5,099,862 A | 3/1992 | White et al. |
| 5,121,757 A | 6/1992 | White et al. |
| 5,131,415 A | 7/1992 | Munoz et al. |
| 5,143,097 A | 9/1992 | Sohn et al. |
| 5,148,819 A | 9/1992 | Fagg |
| 5,159,942 A | 11/1992 | Brinkley et al. |
| 5,197,494 A | 3/1993 | Kramer |
| 5,230,354 A | 7/1993 | Smith et al. |
| 5,234,008 A | 8/1993 | Fagg |
| 5,235,992 A | 8/1993 | Sensabaugh, Jr. |
| 5,243,999 A | 9/1993 | Smith |
| 5,296,621 A | 3/1994 | Roos et al. |
| 5,301,694 A | 4/1994 | Raymond et al. |
| 5,318,050 A | 6/1994 | Gonzalez-Parra et al. |
| 5,343,879 A | 9/1994 | Teague |

(Continued)

FOREIGN PATENT DOCUMENTS

| | | |
|---|---|---|
| CN | 1133694 | 10/1996 |
| CN | 101262786 | 9/2008 |

(Continued)

OTHER PUBLICATIONS

Liu et al. J. Henan Agricult. Sci. 2012. vol. 41, No. 9, pp. 50-52. CABA Abstract enclosed.*

(Continued)

*Primary Examiner* — Chris R Tate

(74) *Attorney, Agent, or Firm* — Womble Carlyle Sandridge & Rice LLP

(57) ABSTRACT

A method for producing lutein from one or more plants of genus *Nicotiana* is provided. The lutein can be derived inter alia from *Nicotiana* species biomass. A method such as is described in various embodiments herein also provides articles and compositions that include lutein produced from one or more plants of genus *Nicotiana*.

16 Claims, No Drawings

(56) References Cited

U.S. PATENT DOCUMENTS

| | | | |
|---|---|---|---|
| 5,360,022 A | 11/1994 | Newton et al. | |
| 5,397,571 A | 3/1995 | Roland et al. | |
| 5,426,220 A | 6/1995 | Baniel et al. | |
| 5,435,325 A | 7/1995 | Clapp et al. | |
| 5,445,169 A | 8/1995 | Brinkley et al. | |
| 5,533,530 A | 7/1996 | Young et al. | |
| 5,715,844 A | 2/1998 | Young et al. | |
| 5,724,998 A | 3/1998 | Gellatly et al. | |
| 5,859,263 A | 1/1999 | Ghorpade et al. | |
| 5,932,095 A | 8/1999 | Walters et al. | |
| 6,083,729 A | 7/2000 | Martin et al. | |
| 6,131,584 A | 10/2000 | Lauterbach | |
| 6,216,706 B1 | 4/2001 | Kumar et al. | |
| 6,225,483 B1 | 5/2001 | Franke | |
| 6,262,284 B1 | 7/2001 | Khachik | |
| 6,298,858 B1 | 10/2001 | Coleman, III et al. | |
| 6,298,859 B1 | 10/2001 | Kierulff et al. | |
| 6,325,860 B1 | 12/2001 | Coleman, III | |
| 6,403,126 B1 | 6/2002 | Webster et al. | |
| 6,414,172 B1 | 7/2002 | Garcés et al. | |
| 6,417,157 B1 | 7/2002 | Wadsworth et al. | |
| 6,428,624 B1 | 8/2002 | Coleman, III et al. | |
| 6,440,223 B1 | 8/2002 | Dube et al. | |
| 6,495,175 B2 | 12/2002 | Rao et al. | |
| 6,499,489 B1 | 12/2002 | Coleman, III | |
| 6,504,085 B1 | 1/2003 | Howard | |
| 6,591,841 B1 | 7/2003 | White et al. | |
| 6,695,924 B1 | 2/2004 | Dube et al. | |
| 6,772,767 B2 | 8/2004 | Mua et al. | |
| 6,800,318 B2 | 10/2004 | Kapila et al. | |
| 6,860,998 B1 | 3/2005 | Wilde | |
| 6,895,974 B2 | 5/2005 | Peele | |
| 7,025,066 B2 | 4/2006 | Lawson et al. | |
| 7,067,718 B2 | 6/2006 | Anai et al. | |
| 7,074,449 B1 | 7/2006 | Holley et al. | |
| 7,156,981 B2 | 1/2007 | Wilde et al. | |
| 7,179,930 B2 | 2/2007 | Bhaskaran et al. | |
| 7,198,808 B2 | 4/2007 | Krasutsky et al. | |
| 7,271,298 B2 | 9/2007 | Xu et al. | |
| 7,337,782 B2 | 3/2008 | Thompson | |
| 7,351,424 B2 | 4/2008 | Ornelas-Cravioto et al. | |
| 7,615,657 B2 | 11/2009 | Bathurst et al. | |
| 7,622,599 B2 | 11/2009 | Swaminathan et al. | |
| 7,629,007 B2 | 12/2009 | Peña | |
| 7,638,314 B2 | 12/2009 | Zappi et al. | |
| 7,652,167 B2 | 1/2010 | Miller et al. | |
| 7,667,068 B2 | 2/2010 | Miller et al. | |
| 7,671,242 B2 | 3/2010 | Losso et al. | |
| 7,741,500 B2 | 6/2010 | Arhancet et al. | |
| 7,820,419 B2 | 10/2010 | Smith et al. | |
| 7,910,209 B2 | 3/2011 | Uchida et al. | |
| 7,943,350 B2 | 5/2011 | Vlasenko et al. | |
| 8,236,929 B2 | 8/2012 | Cheryan et al. | |
| 8,247,423 B2 | 8/2012 | Estok et al. | |
| 8,360,072 B2 | 1/2013 | Krauss | |
| 8,389,749 B2 | 3/2013 | Dumesic et al. | |
| 8,893,725 B2 | 11/2014 | Dube et al. | |
| 2002/0197688 A1 | 12/2002 | Pandolfino | |
| 2004/0111762 A1 | 6/2004 | Anai et al. | |
| 2004/0173228 A1 | 9/2004 | Coleman, III | |
| 2005/0147722 A1 | 7/2005 | Fan et al. | |
| 2006/0003036 A1 | 1/2006 | Shaath et al. | |
| 2007/0137663 A1 | 6/2007 | Taylor et al. | |
| 2007/0193596 A1 | 8/2007 | Mori et al. | |
| 2007/0277432 A1 | 12/2007 | Jackam et al. | |
| 2009/0028803 A1 | 1/2009 | Mishra et al. | |
| 2009/0234146 A1 | 9/2009 | Cooney et al. | |
| 2009/0246525 A1 | 10/2009 | Uchida et al. | |
| 2010/0017916 A1 | 1/2010 | Pappan et al. | |
| 2010/0037903 A1 | 2/2010 | Coleman, III et al. | |
| 2010/0196980 A1 | 8/2010 | Smith et al. | |
| 2010/0197029 A1 | 8/2010 | O'Fallon et al. | |
| 2010/0239726 A1 | 9/2010 | Pertsovich | |
| 2010/0286420 A1 | 11/2010 | Akatsuka et al. | |
| 2011/0083683 A1* | 4/2011 | Krauss | 131/297 |
| 2011/0174323 A1 | 7/2011 | Coleman, III et al. | |
| 2011/0247640 A1 | 10/2011 | Beeson et al. | |
| 2011/0259353 A1 | 10/2011 | Coleman, III et al. | |
| 2012/0040408 A1 | 2/2012 | Decker et al. | |
| 2012/0125354 A1 | 5/2012 | Byrd et al. | |
| 2012/0141648 A1 | 6/2012 | Morton et al. | |
| 2012/0152265 A1 | 6/2012 | Dube et al. | |
| 2012/0192880 A1 | 8/2012 | Dube et al. | |
| 2012/0211016 A1 | 8/2012 | Byrd, Jr. et al. | |
| 2012/0260929 A1 | 10/2012 | Coleman et al. | |
| 2012/0272976 A1 | 11/2012 | Byrd et al. | |
| 2012/0312314 A1 | 12/2012 | Plakidis et al. | |
| 2013/0014771 A1 | 1/2013 | Coleman, III et al. | |
| 2013/0125907 A1 | 5/2013 | Dube et al. | |
| 2013/0276801 A1 | 10/2013 | Byrd, Jr. et al. | |
| 2014/0031592 A1 | 1/2014 | Shinde | |
| 2014/0096780 A1 | 4/2014 | Gerardi | |
| 2014/0271952 A1 | 9/2014 | Mua et al. | |

FOREIGN PATENT DOCUMENTS

| | | |
|---|---|---|
| CN | 101450897 | 6/2009 |
| CN | 101801188 | 8/2010 |
| CN | 102079704 | 6/2011 |
| CN | 10218366 | 9/2011 |
| EP | 0 244 208 | 11/1987 |
| GB | 1 202 821 | 8/1970 |
| GB | 2 020 538 A | 11/1979 |
| JP | 59-28465 A | 2/1984 |
| JP | H08-266260 | 10/1996 |
| JP | 1162008 | 10/1997 |
| JP | H11308987 | 11/1999 |
| JP | H-11332408 | 12/1999 |
| JP | 2003024096 | 1/2003 |
| JP | 2009527488 | 7/2009 |
| KR | 930003904 | 5/1993 |
| KR | 10-2006-0054728 | 5/2006 |
| KR | 1020120022238 | 3/2012 |
| KR | 101233116 | 2/2013 |
| WO | WO 02/083191 | 10/2002 |
| WO | WO 2005/027892 | 3/2005 |
| WO | WO 2008/092207 | 8/2008 |
| WO | WO 2009/075762 | 6/2009 |
| WO | WO 2009/110775 A1 | 9/2009 |
| WO | WO 2010/054198 A2 | 5/2010 |
| WO | WO 2014/138223 * | 9/2014 |

OTHER PUBLICATIONS

Xi et al. Yancao Keji. 2011. vol. 5, pp. 29-33. CAPLUS Abstract enclosed.*

Li et al. Nanfang Nongye Xuebao. 2012. vol. 43, No. 8, pp. 1158-1163. CAPLUS Abstract enclosed.*

Wu et al. Yunnan Nongye Daxue Xuebao. 2013. vol. 28, No. 3, pp. 353-359. CAPLUS Abstract enclosed.*

Alonso et al., "Integrated Conversion of Hemicellulose and Cellulose from Lignocellulosic Biomass," *Energy & Environmental Science*, 2013, vol. 6, pp. 76-80.

Brandt et al., "Practical Aspects of Preparative HPLC in Pharmaceutical and Development Production", *LC•GC Europe*, Mar. 2002, pp. 2-5.

Bryzgalov et al., "Comparative Life Cycle Assessment of General Loose and Portion Snus", *1N1800 Life Cycle Assessment*, May 26, 2005, pp. 3-23.

Chu et al, "Fatty Acid Composition in Tobacco, I. Green Tobacco Plants", Plant Physiology, American Society of Plant Biologists, Mar. 1968; 43(3): 428-433, [online], retrieved from the Internet, [retrieved Jun. 24, 2015], <URL:http://www.ncbi.nlm.nih.gov/pmc/articles/PMC1086856/>.

Clark et al., "Derivatization Solid-Phase Microextraction Gas Chromatographic-Mass Spectrometric Determination of Organic Acids in Tobacco"; 1997; Journal of Chromatographic Science; vol. 35; pp. 209-212.

Coleman, III et al., "Headspace Solid-Phase Microextraction Analysis of Artificial Flavors", *J. Sci. Food Agric.*, 2005, pp. 2645-2654, vol. 85.

(56) References Cited

OTHER PUBLICATIONS

Coleman, III et al., "The Use of a Non-Equilibrated Solid Phase Microextraction Method to Quantitatively Determine the Off-Notes in Mint and Other Essential Oils", *J. Sci. Food Agric.*, 2004, pp. 1223-1228, vol. 84.
Crabbe et al., "Biodiesel Production of Crude Palm Oil and Evaluation of Butanol Extraction and Fuel Properties," *Process Biochemistry*, 37, 65-71, (2001).
"Enzyme Class Index: Hydrolases on esters", Sigma-Aldrich, 2014, [online], Retrieved from the Internet, [retrieved Oct. 21, 2014], <URL: http://www.sigmaaldrich.com/life-science/metabolomics/enzyme-explorer/class-index/hydrolases-on-esters.html>.
Frega et al., "Chemical Composition of Tobacco Seeds (*Nicotiana tobacum L.*)", *JAOCS.*, 1991, vol. 68, No. 1, pp. 29-33.
Giannelos et al., "Tobacco Seed Oil as an Alternative Diesel Fuel: Physical and Chemical Properties", *Industrial Crops and Products*, 2002, vol. 16, pp. 1-9.
Ishikawa et al., "Water-Soluble Constituents of Dill", *Chem. Pharm. Bull.*, 2002, pp. 501-507, vol. 50., No. 4.
Kodama et al., "Isolation of a New Terpene Glucoside, 3-Hydroxy-5, 6-epoxy-β-ionyl-β-D- glucopyranoside from Flue-cured Tobacco", *Agric. Biol. Chem.*, 1981, pp. 941-944, vol. 45, No. 4.
Kolah et al."Reaction Kinetics of the Catalytic Esterification of Citric Acid with Ethanol", 2007; Industrial Engineering and Chemistry Research; vol. 46; pp. 3180-3187; American Chemical Society.
Ejikeme et al., "Catalysis in Biodiesel Production by Trans-Esterification Processes: An Insight," *Journal Chemistry*, 7, 1120-1132 (2010).
Freedman et al., "Trans-Esterification Kinetics of Soybean Oil," *JAOCS*, 63, 1375-1380 (1986).
Kolah et al. (2008), "Triethyl Citrate Synthesis by Reactive Distillation," *Industrial and Engineering Chemistry Research*, vol. 47, No. 4, pp. 1017-1024.
Leffingwell & Associates, Ester Detection Thresholds and Molecular Structures, www.leffmgwell.com/esters, downloaded Sep. 23, 2015.
Leffingwell et al., "Tobacco Flavoring for Smoking Products", *R. J. Reynolds Tobacco Company*, 1972, pp. 1-72.
Loughrin et al., "Headspace Compounds from Flowers of *Nicotiana tabacum* and Related Species", *J. Agric. Food Chem.*, 1990, vol. 38, No. 2, pp. 455-460.
Loughrin et al., "Glycosidically Bound Volatile Components of *Nicotiana Sylvestris* and *N. Suaveolens Flowers*", *Phytochemistry*, 1992, pp. 1537-1540, vol. 31, No. 5.
Marchetti et al.,: "Possible Methods for Biodiesel Production"; Renewable and Sustainable Energy Review; pp. 1300-1311; vol. 11; No. 6; 2007; US.
Matsumura et al., "Water-Soluble Constituents of Caraway: Carvone Derivatives and their Glucosides", *Chem. Pharm, Bull.*, 2002, pp. 66-72, vol. 50, No. 1.
Matsuzake et al.; "Novel Glycerolipids and Glycolipids from the Surface Lipids of Nicotiana Benthamiana". Biosci. Biotech_Biochem; Mar. 1992; pp. 1565-1569; vol. 56; No. 10; JP.
Moldoveanu et al., "Dual Analysis of Triglycerides from Certain Common Lipids and Seed Extracts," *J Agric.Food Chem.*, 59, 2137-2147 (2011).
Moldoveanu, "5. Profiling of lipids from fruit and seed extracts", Lipidomics: Sea Food, Marine Based Dietary Supplement, Fruit and Seed, 2012: pp. 73-123, Ed. Su Chen [online], Retrieved from the Internet, [retrieved Oct. 21, 2014], <URL: http://www.trnres.com/ebook/uploads/suchencontent/T_137431930851/020Su%20Chen.pdf>.
Mukhtar et al., "Fatty Acid Composition of Tobacco Seed Oil and Synthesis of Alkyd Resin", *Chin. J. of Chem.*, 2007, vol. 25, No. 5, pp. 705-708.
Satynaryana Murthy, "Performance of Tobacco Oil Based Bio-Diesel Fuel in a Single cylinder Direct Injection Engine," *International J. Physical Sci.*, 5, 2066-2074 (2010).

Ochiai, N., "6 Times Faster Screening of Pesticide Multi-Residues in Aqueous Samples Take Two!" *Gerstel Solutions Worldwide*, 2006, pp. 17-19, No. 6.
Patel et al., "Production Potential and Quality Aspects of Tobacco Seed Oil", *Tob. Res.*, 1998, vol. 24, No. 1, pp. 44-49.
Perflavory Information System, www.perflavory.com, downloaded Sep. 23, 2015.
Raguso et al., "Fragrance Chemistry, Nocturnal Rhythms and Pollination "Syndromes" in *Nicotiana*", *Phytochemisny*, 2003, pp. 265-284, vol. 63.
Ralph et al., "NMR Characterization of Altered Lignins Extracted from Tobacco Plants Down-Regulated for Lignification Enzymes Cinnamyl-Alcohol Dehydrogenase and Cinnamoyl-CoA Reductase" *Proceedings of the National Academy of Sciences*, 1998, vol. 95, pp. 12803-12808, http://www.ncbi.nlm.nih.gov/pinc/articles/PMC23601/.
Sadecka, et al.; Determination of organic acids in tobacco by capillary isotachophoresis; 2003; Journal of Chromatography A; vol. 988; pp. 161-165; Elsevier Science B.V.
Sahraoui et al., "Improved Microwave Steam Distillation Apparatus for Isolation of Essential Oils Comparison with Conventional Steam Distillation", *J. Chromatogr. A.*, 2008, pp. 229-233.
Schuchardt et al., "Trans-Esterification of Vegetable Oils: A Review," Chem. Soc., 9, 199-210 (1998).
Shmuk et al. (1930), "Investigation of the Tobacco Acids," in Works of Academician A.A. Shmuk, vol. III, The Chemistry and Technology of Tobacco (Moscow: Pishchepromidzat, 1953; Jerusalem: trans. Lengy et al., Israel Program for Scientific Translations, 1961), pp. 136-144,.
Shmuk et al. (1933), "Tobacco and Makhorka As Raw Materials for the Production of Citric Acid," in Works, op. cit., pp. 688-707.
Shmuk (1934), "The Method of Determination of Citric and Malic Acids in Tobacco and Makhorka," Ibid., pp. 247-251.
Snook et al., "The Flower Flavonols of *Nicotiana Species*", *Phytochemistry*, 1992, pp. 1639-1647, vol. 31, No. 5.
Stanisavljevic et al., "Comparison of techniques for the Extraction of Tobacco Seed Oil", *Eur. J. Lipid Sci. Technol.*, 2009, vol. 111, pp. 513-518.
Stanisavljevićet al., Ultrasonic extraction of oil from tobacco (*Nicotiana tabacwn*L.) seeds, *Ultrasonics Sonochemistry*, 2007, pp. 646-652, vol. 14, No. 5.
Stanesh, Biochemistry, Chapter 6. Lipids and Membranes, Springer Science+Business Media, 1998, pp. 141-144.
Tienpont et al., "Stir Bar Sorptive Extraction-Thermal Desorption-Capillary GC-MS Applied to Biological Fluids", *Anal. Bioanal. Chem..*, 2002, pp. 46-55, vol. 373.
TSO (1972), Physiology and Biochemistry of Tobacco Plants (Stroudsburg: Dowden, Hutchinson and Ross), p. 205.
Veljkovic V B et al.; "Biodiesel Production from Tobacco Seed Oil with a High Content of Free Fatty Acids"; Fuel, IPC Science and Technology Press; pp. 2671-2675; vol. 85; No. 17; GB.
Vickery et al. The Non-Volatile Organic Acids of Green Tobacco Leaves; 1931; Journal of Biological Chemistry; vol. 90; pp. 637-653.
Winayanuwattikun P et all; "Potential Plant Oil Feedstock for Lipase-Catalyzed Biodiesel Production in Thailand"; Biomass and Bioenergy; pp. 1279-1286; vol. 32; No. 12; 2008; Amsterdam, NL.
Zhang, Yi-Heng Percival et al., Toward an Aggregated Understanding of Enzymatic Hydrolysis of Cellulose: Noncomplexed Cellulase Systems. Wiley InterScience. Biotechnology and Bioengineering, vol. 88, No. 7, Dec. 30, 2004, pp. 797-824.
Zhang et al., "Advances in the Catalytic Production and Utilization of Sorbitol," *Industrial & Engineering Chemisuy Research*, 2013, vol. 52, pp. 11799-11815.
Ziaie-Shirkolaee et al. "Study on Cellulose Degradation During Organosolv Delignification of Wheat Straw and Evaluation of Pulp Properties," *Iranian Polymer Journal*, 2007, pp. 83-96, vol. 16, (2).

* cited by examiner

METHOD FOR PRODUCING LUTEIN FROM TOBACCO

FIELD OF THE INVENTION

A method such as is described in various embodiments herein relates to products comprising lutein made or derived from tobacco or, more generally, made or derived from any biomass derived from any one or more species of genus *Nicotiana*, or that otherwise incorporate tobacco. Of particular interest are products comprising lutein obtained or derived from plants or portions of plants from the *Nicotiana* species.

BACKGROUND OF THE INVENTION

Popular smoking articles, such as cigarettes, have a substantially cylindrical rod shaped structure and include a charge, roll or column of smokable material such as shredded tobacco (e.g., in cut filler form) surrounded by a paper wrapper thereby forming a so-called "tobacco rod." Normally, a cigarette has a cylindrical filter element aligned in an end-to-end relationship with the tobacco rod. Typically, a filter element comprises plasticized cellulose acetate tow circumscribed by a paper material known as "plug wrap." Certain cigarettes incorporate a filter element having multiple segments, and one of those segments can comprise activated charcoal particles. Typically, the filter element is attached to one end of the tobacco rod using a circumscribing wrapping material known as "tipping paper." It also has become desirable to perforate the tipping material and plug wrap, in order to provide dilution of drawn mainstream smoke with ambient air. A cigarette is employed by a smoker by lighting one end thereof and burning the tobacco rod. The smoker then receives mainstream smoke into his/her mouth by drawing on the opposite end (e.g., the filter end) of the cigarette.

The tobacco used for cigarette manufacture is typically used in blended form. For example, certain popular tobacco blends, commonly referred to as "American blends," comprise mixtures of flue-cured tobacco, burley tobacco, and Oriental tobacco, and in many cases, certain processed tobaccos, such as reconstituted tobacco and processed tobacco stems. The precise amount of each type of tobacco within a tobacco blend used for the manufacture of a particular cigarette brand varies from brand to brand. However, for many tobacco blends, flue-cured tobacco makes up a relatively large proportion of the blend, while Oriental tobacco makes up a relatively small proportion of the blend. See, for example, *Tobacco Encyclopedia*, Voges (Ed.) p. 44-45 (1984), Browne, *The Design of Cigarettes*, $3^{rd}$ Ed., p. 43 (1990) and *Tobacco Production, Chemistry and Technology*, Davis et al. (Eds.) p. 346 (1999).

Through the years, various treatment methods and additives have been proposed for altering the overall character or nature of tobacco materials utilized in tobacco products. For example, additives or treatment processes have been utilized in order to alter the chemistry or sensory properties of the tobacco material, or in the case of smokable tobacco materials, to alter the chemistry or sensory properties of mainstream smoke generated by smoking articles including the tobacco material. The sensory attributes of cigarette smoke can be enhanced by incorporating flavoring materials into various components of a cigarette. Exemplary flavoring additives include menthol and products of Maillard reactions, such as pyrazines, aminosugars, and Amadori compounds. See also, Leffingwell et al., *Tobacco Flavoring for Smoking Products*, R.J. Reynolds Tobacco Company (1972), which is incorporated herein by reference. In some cases, treatment processes involving the use of heat can impart to the processed tobacco a desired color or visual character, desired sensory properties, or a desired physical nature or texture. Various processes for preparing flavorful and aromatic compositions for use in tobacco compositions are set forth in U.S. Pat. No. 3,424,171 to Rooker; U.S. Pat. No. 3,476,118 to Luttich; U.S. Pat. No. 4,150,677 to Osborne, Jr. et al.; U.S. Pat. No. 4,986,286 to Roberts et al.; U.S. Pat. No. 5,074,319 to White et al.; U.S. Pat. No. 5,099,862 to White et al.; U.S. Pat. No. 5,235,992 to Sensabaugh, Jr.; U.S. Pat. No. 5,301,694 to Raymond et al.; U.S. Pat. No. 6,298,858 to Coleman, III et al.; U.S. Pat. No. 6,325,860 to Coleman, III et al.; U.S. Pat. No. 6,428,624 to Coleman, III et al.; U.S. Pat. No. 6,440,223 to Dube et al.; U.S. Pat. No. 6,499,489 to Coleman, III; U.S. Pat. No. 6,591,841 to White et al.; and U.S. Pat. No. 6,695,924 to Dube et al.; and US Pat. Appl. Publication Nos. 2004/0173228 to Coleman, III and 2010/0037903 to Coleman, III et al., each of which is incorporated herein by reference. Additionally, examples of representative components that can be employed as so-called natural tar diluents in tobacco products are set in PCT WO 07/012,980 to Lipowicz, which is incorporated herein by reference.

Tobacco also may be enjoyed in a so-called "smokeless" form. Particularly popular smokeless tobacco products are employed by inserting some form of processed tobacco or tobacco-containing formulation into the mouth of the user. Various types of smokeless tobacco products are set forth in U.S. Pat. No. 1,376,586 to Schwartz; U.S. Pat. No. 3,696,917 to Levi; U.S. Pat. No. 4,513,756 to Pittman et al.; U.S. Pat. No. 4,528,993 to Sensabaugh, Jr. et al.; U.S. Pat. No. 4,624,269 to Story et al.; U.S. Pat. No. 4,987,907 to Townsend; U.S. Pat. No. 5,092,352 to Sprinkle, III et al.; U.S. Pat. No. 5,387,416 to White et al.; and U.S. Pat. No. 8,336,557 to Kumar et al.; US Pat. Appl. Pub. Nos. 2005/0244521 to Strickland et al. and 2008/0196730 to Engstrom et al.; PCT WO 04/095959 to Arnarp et al.; PCT WO 05/063060 to Atchley et al.; PCT WO 05/016036 to Bjorkholm; and PCT WO 05/041699 to Quinter et al., each of which is incorporated herein by reference. See, for example, the types of smokeless tobacco formulations, ingredients, and processing methodologies set forth in U.S. Pat. No. 6,953,040 to Atchley et al. and U.S. Pat. No. 7,032,601 to Atchley et al., each of which is incorporated herein by reference.

One type of smokeless tobacco product is referred to as "snuff." Representative types of moist snuff products, commonly referred to as "snus," have been manufactured in Europe, particularly in Sweden, by or through companies such as Swedish Match AB, Fiedler & Lundgren AB, Gustavus AB, Skandinavisk Tobakskompagni A/S, and Rocker Production AB. Snus products available in the U.S.A. have been marketed under the tradenames Camel Snus Frost, Camel Snus Original and Camel Snus Spice by R. J. Reynolds Tobacco Company. See also, for example, Bryzgalov et al., 1N1800 Life Cycle Assessment, Comparative Life Cycle Assessment of General Loose and Portion Snus (2005). In addition, certain quality standards associated with snus manufacture have been assembled as a so-called GothiaTek standard. Representative smokeless tobacco products also have been marketed under the tradenames Oliver Twist by House of Oliver Twist A/S; Copenhagen, Skoal, SkoalDry, Rooster, Red Seal, Husky, and Revel by U.S. Smokeless Tobacco Co.; "taboka" by Philip Morris USA; Levi Garrett, Peachy, Taylor's Pride, Kodiak, Hawken Wintergreen, Grizzly, Dental, Kentucky King, and Mammoth Cave by Conwood Company, LLC; and Camel Orbs, Camel Sticks, and Camel Strips by R. J. Reynolds Tobacco Company.

The sensory attributes of smokeless tobacco can also be enhanced by incorporation of certain flavoring materials. See, for example, U.S. Pat. No. 6,668,839 to Williams; U.S. Pat. No. 6,834,654 to Williams; U.S. Pat. No. 7,032,601 to Atchley et al.; U.S. Pat. No. 7,694,686 to Atchley et al.; U.S. Pat. No. 7,861,728 to Holton, Jr. et al.; U.S. Pat. No. 7,819,124 to Strickland et al.; U.S. Pat. No. 7,810,507 to Dube et al.; and U.S. Pat. No. 8,168,855 to Nielsen et al; US Pat. Appl. Pub. Nos. 2004/0020503 to Williams, 2006/0191548 to Strickland et al.; 2007/0062549 to Holton, Jr. et al.; 2008/0029116 to Robinson et al.; 2008/0029117 to Mua et al.; and 2008/0173317 to Robinson et al., each of which is incorporated herein by reference.

Among the many constituents of tobacco is lutein (CAS 127-40-2). See, for example, Tso, *Physiology and Biochemistry of Tobacco Plants*, pp. 209, 212 (1972). Lutein has a molecular weight of about 568.87 and is also known, for example, as xanthophyll; or (3R,3'R,6R)-4,5-didehydro-5,6-dihydro-β,β-carotene-3,3'-diol. While it may serve any of a number of functions in tobacco product formulations, lutein is known in the art to serve as an antioxidant, an anti-inflammatory agent, an agent to prevent and/or ameliorate age-related macular degeneration, and an agent counteracting the deleterious effects of certain polycyclic aromatic hydrocarbons subject to activation by one or more cytochrome P450 monooxygenases. At typical room temperature, lutein is yellowish in color and may have the microscopic appearance of prisms. Lutein is essentially insoluble in water and has a melting point of less than 200° C.

Methods for producing lutein are known in the art. U.S. Pat. No. 6,262,284 to Khachik teaches a method for the extraction and saponification of lutein esters from a plant source comprising extraction with a solution containing tetrahydrofuran and an alcohol with the addition of potassium or sodium hydroxide to maintain the pH at 12. U.S. Pat. No. 7,253,294 to Hoffman et al. teaches isolating lutein by inter alia heating a syrup derived from macerated alfalfa green plants, separating a solid fraction from the syrup, then extracting, saponifying and further extracting the solid fraction. U.S. Pat. No. 7,271,298 to Xu et al. teaches a process for preparing xanthophylls such as lutein comprising saponifying a plant oleoresin with an alcohol at 40-85° C. and adjusting the pH of the resultant mixture to pH 1-7. U.S. Pat. No. 7,351,424 to Ornelas-Cravioto et al. teaches inter alia a composition comprising at least 85% by weight of xanthophyll esters, wherein the xanthophyll esters are comprised of at least 94% of trans-lutein esters. U.S. Pat. No. 7,622,599 to Swaminathan et al. teaches producing lutein-enriched carteonoids by inter alia anaerobically ensilaging Marigold flower petals, hexane extraction of meal derived therefrom, and hot water washing of the extract. U.S. Pat. No. 7,629,007 to Pena teaches isolating a xanthophyll such as lutein by inter alia preparing and saponifying a plant-derived oleoresin, washing the saponified oleoresin with a salt solution until the pH of the resin is about 6.5 to 9, and washing the resin with a non-polar solvent and with an increased polarity solvent. U.S. Pat. No. 8,236,929 to Cheryan et al. teaches obtaining xanthophylls such as lutein by extracting corn with warm ethanol. U.S. Pat. No. 7,671,242 to Losso et al. teaches isolating aflatoxin-free lutein by inter alia treating a ground plant source with acetone. US Pat. Appl. Pub. No. 2012/0141648 to Morton et al. teaches homogenizing plant material in the presence of an extraction solvent to form a combination of a plant liquid component and a plant pulp component such that the plant liquid component is provided with a pH in a defined range; withdrawing the plant liquid component from the plant pulp component; and separating the liquid plant component into a solids fraction and a soluble fraction. US Pat. Appl. Pub. No. 2012/0272976 to Byrd et al. teaches a method of extracting and isolating lutein from tobacco material comprising contacting the tobacco material with a solvent for a time and under conditions sufficient to extract lutein from the plant material into the solvent; separating the solvent containing lutein from the extracted tobacco material; and purifying the solvent containing lutein to provide an isolate comprising at least about 75 percent by weight lutein. Each of the foregoing is incorporated herein by reference.

While methods for producing lutein are known in the art, facile methods for producing lutein from tobacco that do not employ extremes of temperature or pH are not. There is a long-felt need for a method for producing lutein from a plant source whose agronomic properties are well-characterized and favorable, such as tobacco, from which considerable per-plant biomass is produced during a single growing season. More generally, there is a long-felt need for an environmentally favorable process for the preparation of such a valuable constituent as lutein.

As it should be clear from the foregoing that lutein is useful not only as a constituent of various tobacco products but also an antioxidant, an anti-inflammatory agent, an agent to prevent and/or ameliorate age-related macular degeneration, and an agent counteracting the deleterious effects of certain polycyclic aromatic hydrocarbons subject to activation by one or more cytochrome P450 monooxygenases, it can also be seen that it would accordingly be desirable to provide a method for producing lutein from tobacco, that is, in particular, from *Nicotiana* species, for use, inter alia, in tobacco compositions utilized in a variety of tobacco products or in the processing of tobacco, or more generally in compositions that may comprise an antioxidant, an anti-inflammatory agent, an agent to prevent and/or ameliorate age-related macular degeneration, and/or an agent counteracting the deleterious effects of certain polycyclic aromatic hydrocarbons subject to activation by one or more cytochrome P450 monooxygenases.

SUMMARY OF THE INVENTION

A method such as is described in various embodiments herein provides materials from *Nicotiana* species (e.g., tobacco-derived materials) comprising isolated components from plants of the *Nicotiana* species useful for incorporation into tobacco compositions utilized in a variety of tobacco products, such as smoking articles and smokeless tobacco products, or more generally into compositions that may comprise an antioxidant, an anti-inflammatory agent, an agent to prevent and/or ameliorate age-related macular degeneration, and/or an agent counteracting the deleterious effects of certain polycyclic aromatic hydrocarbons subject to activation by one or more cytochrome P450 monooxygenases. A method such as is described in various embodiments herein also provides methods for isolating components from *Nicotiana* species (e.g., tobacco materials), and methods for processing those components and tobacco materials incorporating those components. For example, tobacco-derived materials can be prepared by subjecting at least a portion of a tobacco plant (e.g., leaves, stalks, roots, or stems) to a separation process, which typically can include multiple sequential extraction steps, in order to isolate desired components of the tobacco material. For example, tobacco-derived materials can be prepared by subjecting at least a portion of a tobacco plant (e.g., leaves, stalks, roots, or stems) to a separation process, which typically can include multiple sequential extraction steps, in order to isolate desired components of the tobacco material.

When used in connection with a method such as is described in various embodiments herein, the term "biomass" denotes one or more portions of a plant, and in particular denotes substantially the entirety of the superterranean portion of a plant, optionally including some or all of the subterranean portion of a plant. Accordingly, the term "biomass" may refer to leaf or to seed or to any other superterranean portion of a plant, or to any combination thereof, optionally including some or all of the subterranean portion of a plant. Accordingly, the term "biomass" and related terms such as "biomatter" and "plant source" may be properly understood to refer to any one or more portions of a harvested plant that may be processed to extract, separate, or isolate components of interest therefrom.

When used in connection with a method such as is described in various embodiments herein, the term "one or more plants of genus *Nicotiana*" denotes any one or more plants of the genus *Nicotiana* of family Solanaceae, including, for example, any one or more of the following: *N. alata, N. arentsii, N. excelsior, N. forgetiana, N. glauca, N. glutinosa, N. gossei, N. kawakamii, N. knightiana, N. langsdorffi, N. otophora, N. setchelli, N. sylvestris, N. tomentosa, N. tomentosiformis, N. undulata,* and *N. sanderae, N. africana, N. amplexicaulis, N. benavidesii, N. bonariensis, N. debneyi, N. longiflora, N. maritina, N. megalosiphon, N. occidentalis, N. paniculata, N. plumbaginifolia, N. raimondii, N. rosulata, N. rustica, N. simulans, N. stocktonii, N. suaveolens, N. tabacum, N. umbratica, N. velutina,* and *N. wigandioides, N. acaulis, N. acuminata, N. attenuata, N. benthamiana, N. cavicola, N. clevelandii, N. cordifolia, N. corymbosa, N. fragrans, N. goodspeedii, N. linearis, N. miersii, N. nudicaulis, N. obtusifolia, N. occidentalis* subsp. *Hersperis, N. pauciflora, N. petunioides, N. quadrivalvis, N. repanda, N. rotundifolia, N. Solanifolia, N. spegazzinii.*

When used in connection with a method such as is described in various embodiments herein, "alkali metal hydroxide" denotes any one or more of the compounds having formula MOH where M is Li, Na, K, Rb, Cs, or Fr.

When used in connection with a method such as is described in various embodiments herein, "mineral acid" denotes an inorganic acid and accordingly can refer, for example, to any one or more of the following: sulfuric acid; phosphoric acid; nitric acid; chloric acid; hydrofluoric acid; hydrochloric acid; hydrobromic acid; hydroiodic acid; chromic acid; sulfurous acid; phosphorous acid; nitrous acid; a halogensulfonic acid $HSO_3X$ wherein X is halogen; perchloric acid; perbromic acid; periodic acid; hydrogen sulfide; hypophosphorous acid; tetrafluoroboric acid; hexafluorophosphoric acid.

The use of *Nicotiana*-derived (e.g., tobacco-derived) materials produced by a method such as is described in various embodiments herein enables the preparation of tobacco compositions for smoking articles or smokeless tobacco compositions that are derived substantially or even entirely from *Nicotiana* materials. For example, a tobacco composition can incorporate tobacco or tobacco-derived material of some form, including isolated components from *Nicotiana* species, such that at least about 80 weight percent, more typically at least about 90 weight percent, or even at least about 95 weight percent (on a dry weight basis), of that tobacco composition consists of tobacco-derived material.

It has long been recognized that there is a need to make fuller use of material or substance from tobacco, and in particular from plants or portions of plants from the *Nicotiana* species. Readily available starting materials or inputs from plants or portions of plants from the *Nicotiana* species, such starting materials or inputs being useful in particular for inclusion as starting materials or inputs in a process whereby material or substance from tobacco can be more fully utilized, include inter alia tobacco biomass. Tobacco biomass can include for example the entirety of the substance of a tobacco plant that has been harvested whole. Tobacco biomass can include for example essentially all of the superterranean parts of a tobacco plant and optionally can include some or all of the subterranean parts of a tobacco plant. Tobacco biomass can include for example the solid portion of a tobacco plant that has been harvested whole, or the solid portion of essentially all of superterranean parts of a tobacco plant, and from which so-called "green juice" has been expelled for example through the action of a screw press. Tobacco biomass can include for example such a solid portion from which at least a portion of the water has been removed by drying.

Among ways in which fuller use can be made of material or substance from tobacco, and in particular from plants or portions of plants from the *Nicotiana* species, are various phyisical and/or chemical transformations to which plants or portions of plants from the *Nicotiana* species can be subjected. Such physical and/or chemical transformations may result in outputs or products having one or more desired or favorable properties. Such outputs or products may themselves be useful as starting material or inputs for further useful processes. Among physical transformations to which plants or portions of plants from the *Nicotiana* species can be subjected are disruptions of the physical integrity of tobacco biomass, such as a disruption resulting from the action of a screw press against a quantity of tobacco biomass. Among physical transformations to which plants or portions of plants from the *Nicotiana* species can be subjected are fractionations according to, for example, particle size, relative density, sedimentation velocity, or affinity for a fixed matrix. Among chemical transformations to which plants or portions of plants from the *Nicotiana* species can be subjected are hydrolyses, including, for example, acid-catalyzed hydrolyses and base-catalyzed hydrolyses. Acid-catalyzed hydrolyses of esters and base-catalyzed hydrolyses of esters are known in the art. An ester which may be subject to hydrolysis includes an ester found at the sn-1, sn-2 or sn-3 position of a triacylglycerol, of a diacylglycerol, or of a monoacylglycerol, such as, in particular, a triacylglycerol, diacylglycerol or monoacylglycerol present in or derived from a tobacco plant or any portion thereof, including, for example, tobacco biomass, or an ester of lutein, present in or derived from a tobacco plant or any portion thereof, including, for example, tobacco biomass.

Various embodiments of hydrolyses of esters, including acid-catalyzed hydrolyses of esters and base-catalyzed hydrolyses of esters, are known in the art. An acid suitable for an acid-catalyzed hydrolysis of an ester, such as an ester in a triacylglycerol, a diacylglycerol, or a monoacylclycerol, may be a mineral acid. A base suitable for a base-catalyzed hydrolysis of an ester, such as an ester in a triacylglycerol, a diacylglycerol, or a monoacylclycerol, may be a hydroxide of a Group 1 alkali metal monovalent cation, such as lithium hydroxide, sodium hydroxide, or potassium hydroxide.

A method such as is described in various embodiments herein provides a process for isolating lutein from a quantity of tobacco plant material. The tobacco plant material may comprise tobacco biomass.

According to a method such as is described in various embodiments herein, a quantity of tobacco biomass, and in particular a quantity of tobacco biomass that has been subjected to a physical transformation whereby the physical integrity of the biomass is disrupted, such as by maceration and/or one or more other applications of force whereby a plurality of particles of tobacco biomass is formed, may be contacted with an aqueous mixture, such as at a mass ratio of from about 0.1:1 to about 1:1 of aqueous mixture to plant biomass, thereby forming a pigmented slurry. The aqueous mixture may comprise a solution comprising, for example, glycine and one or more compounds selected from the group consisting of salts of phosphoric acid, bisulfite containing compounds, metabisulfite containing compounds, Group I and Group II halide salts, and combinations thereof. The pigmented slurry may be pressed whereupon is formed a pressed solid and a released syrup. The released syrup may be fractionated by application of force, including, for example, centrifugal force, whereupon the released syrup is divided into a component having a lesser sedimentation velocity and a component having a higher sedimentation velocity. A quantity of an acid may be contacted with a quantity of the released syrup component having a lesser sedimentation velocity, whereupon is formed an acidified released syrup component, having a pH of, for example, about 5.9. A quantity of the acidified released syrup component may be contacted with a quantity of diatomaceous earth, whereupon is formed a second pigmented slurry. The second pigmented slurry may be subjected to filtration or otherwise divided whereupon are formed a predominantly solid second pigmented slurry component and a predominantly liquid second pigmented slurry component. A composition comprising a quantity of at least one member of the set consisting of the released syrup component having a higher sedimentation velocity and the predominantly solid second pigmented slurry component may be contacted with a composition comprising at least one solvent in which lutein is soluble, whereupon is formed a pigmented mixture. A quantity of the pigmented mixture may be subjected to filtration or otherwise divided, whereupon are formed a fraction enriched in lutein and the at least one solvent and a fraction in which lutein and the at least one solvent are less abundant. Lutein in the fraction enriched in lutein and the at least one solvent may be separated from the at least one solvent in the fraction enriched in lutein and the at least one solvent, whereupon lutein is isolated.

Accordingly, in an aspect, a method such as is described in various embodiments herein provides a method of producing lutein from tobacco. Such lutein is suitable for use in, on, or around a smoking article or a smokeless tobacco composition comprising a tobacco material and a component derived from the *Nicotiana* species, wherein the component is derived from the *Nicotiana* species. Such lutein is suitable for use more generally in compositions that may comprise an antioxidant, an anti-inflammatory agent, an agent to prevent and/or ameliorate age-related macular degeneration, and/or an agent counteracting the deleterious effects of certain polycyclic aromatic hydrocarbons subject to activation by one or more cytochrome P450 monooxygenases.

DETAILED DESCRIPTION

A method such as is described in various embodiments herein now will be described more fully hereinafter. A method such as is described in various embodiments herein may, however, be embodied in many different forms and should not be construed as limited to the embodiments set forth herein; rather, these embodiments are provided so that this disclosure will be thorough and complete, and will fully convey the scope of a method such as is described in various embodiments herein to those skilled in the art. As used in this specification and the claims, the singular forms "a," "an," and "the" include plural referents unless the context clearly dictates otherwise. Reference to "dry weight percent" or "dry weight basis" refers to weight on the basis of dry ingredients (i.e., all ingredients except water).

The selection of the plant from the *Nicotiana* species can vary; and in particular, the types of tobacco or tobaccos may vary. Tobaccos that can be employed include flue-cured or Virginia (e.g., K326), burley, sun-cured (e.g., Indian Kurnool and Oriental tobaccos, including Katerini, Prelip, Komotini, Xanthi and Yambol tobaccos), Maryland, dark, dark-fired, dark air cured (e.g., Passanda, Cubano, Jatin and Bezuki tobaccos), light air cured (e.g., North Wisconsin and Galpao tobaccos), Indian air cured, Red Russian and Rustica tobaccos, as well as various other rare or specialty tobaccos. Descriptions of various types of tobaccos, growing practices and harvesting practices are set forth in *Tobacco Production, Chemistry and Technology*, Davis et al. (Eds.) (1999), which is incorporated herein by reference. Various representative types of plants from the *Nicotiana* species are set forth in Goodspeed, *The Genus Nicotiana* (Chronica Botanica, 1954); U.S. Pat. No. 4,660,577 to Sensabaugh, Jr. et al.; U.S. Pat. No. 5,387,416 to White et al.; U.S. Pat. No. 7,025,066 to Lawson et al.; U.S. Pat. No. 7,798,153 to Lawrence, Jr.; and U.S. Pat. No. 8,186,360 to Marshall et al., each of which is incorporated herein by reference. Of particular interest are *N. alata, N. arentsii, N. excelsior, N. forgetiana, N. glauca, N. glutinosa, N. gossei, N. kawakamii, N. knightiana, N. langsdorffi, N. otophora, N. setchelli, N. sylvestris, N. tomentosa, N. tomentosiformis, N. undulata*, and *N.×sanderae*. Also of interest are *N. africana, N. amplexicaulis, N. benavidesii, N. bonariensis, N. debneyi, N. longiflora, N. maritina, N. megalosiphon, N. occidentalis, N. paniculata, N. plumbaginifolia, N. raimondii, N. rosulata, N. rustica, N. simulans, N. stocktonii, N. suaveolens, N. tabacum, N. umbratica, N. velutina*, and *N. wigandioides*. Other plants from the *Nicotiana* species include *N. acaulis, N. acuminata, N. attenuata, N. benthamiana, N. cavicola, N. clevelandii, N. cordifolia, N. corymbosa, N. fragrans, N. goodspeedii, N. linearis, N. miersii, N. nudicaulis, N. obtusifolia, N. occidentalis* subsp. *Hersperis, N. pauciflora, N. petunioides, N. quadrivalvis, N. repanda, N. rotundifolia, N. solanifolia* and *N. spegazzinii*.

*Nicotiana* species can be derived using genetic-modification or crossbreeding techniques (e.g., tobacco plants can be genetically engineered or crossbred to increase or decrease production of certain components or to otherwise change certain characteristics or attributes). See, for example, the types of genetic modifications of plants set forth in U.S. Pat. No. 5,539,093 to Fitzmaurice et al.; U.S. Pat. No. 5,668,295 to Wahab et al.; U.S. Pat. No. 5,705,624 to Fitzmaurice et al.; U.S. Pat. No. 5,844,119 to Weigl; U.S. Pat. No. 6,730,832 to Dominguez et al.; U.S. Pat. No. 7,173,170 to Liu et al.; U.S. Pat. No. 7,208,659 to Colliver et al.; and U.S. Pat. No. 7,230,160 to Benning et al.; US Patent Appl. Pub. No. 2006/0236434 to Conkling et al.; and PCT WO 08/103,935 to Nielsen et al. For the preparation of smokeless and smokable tobacco products, it is typical for harvested plants of the *Nicotiana* species to be subjected to a curing process. Descriptions of various types of curing processes for various types of tobaccos are set forth in *Tobacco Production, Chemistry and Technology*, Davis et al. (Eds.) (1999). Exemplary techniques and conditions for curing flue-cured tobacco are set forth in Nestor et al., *Beitrage Tabakforsch. Int.*, 20, 467-475 (2003) and U.S. Pat. No. 6,895,974 to Peele, which are incorporated herein by reference. See, also, for example, U.S. Pat. No. 7,650,892 to Groves et al., which is incorporated herein by reference. Representative techniques and conditions for air curing tobacco are set forth in Roton et al., *Beitrage Tabakforsch. Int.*, 21, 305-320 (2005) and Staaf et al., *Beitrage Tabakforsch. Int.*, 21, 321-330 (2005), which are incorporated herein by reference. Certain types of tobaccos can be subjected to alternative types of curing processes, such as fire curing or sun curing. Preferably, harvested tobaccos that are cured are then aged.

At least a portion of the plant of the *Nicotiana* species (e.g., at least a portion of the tobacco portion) can be employed in an immature form. That is, the plant, or at least one portion of that plant, can be harvested before reaching a stage normally regarded as ripe or mature. As such, for example, tobacco can be harvested when the tobacco plant is at the point of a sprout, is commencing leaf formation, is commencing seeding, is commencing flowering, or the like.

At least a portion of the plant of the *Nicotiana* species (e.g., at least a portion of the tobacco portion) can be employed in a mature form. That is, the plant, or at least one portion of that plant, can be harvested when that plant (or plant portion) reaches a point that is traditionally viewed as being ripe, over-ripe or mature. As such, for example, through the use of tobacco harvesting techniques conventionally employed by farmers, Oriental tobacco plants can be harvested, burley tobacco plants can be harvested, or Virginia tobacco leaves can be harvested or primed by stalk position. After harvest, the plant of the *Nicotiana* species, or portion thereof, can be used in a green form (e.g., tobacco can be used without being subjected to any curing process). For example, tobacco in green form can be frozen, freeze-dried, subjected to irradiation, yellowed, dried, cooked (e.g., roasted, fried or boiled), or otherwise subjected to storage or treatment for later use. Such tobacco also can be subjected to aging conditions.

In accordance with a method such as is described in various embodiments herein, a tobacco product may incorporate tobacco that is combined with some form of biomass or one or more anatomical parts obtained from, or derived from, a plant of at least one *Nicotiana* species. That is, a portion of a tobacco product according to a method such as is described in various embodiments herein can be composed of some form of biomass or one or more anatomical parts of a *Nicotiana* species, such as parts or pieces of biomass or one or more anatomical parts, or processed materials incorporating processed biomass or one or more anatomical parts or components thereof. At least a portion of the tobacco product can be composed of components of biomass or one or more anatomical parts, such as ingredients removed from biomass or one or more anatomical parts (e.g., by extraction, distillation, or other types of processing techniques). At least a portion of the tobacco product can be composed of components derived from biomass or one or more anatomical parts, such as components collected after subjecting biomass or one or more anatomical parts to chemical reaction or after subjecting components collected from biomass or one or more anatomical parts to chemical reaction (e.g., acid/base reaction conditions or enzymatic treatment).

The *Nicotiana* species can be selected for the type of biomass or anatomical part that it produces. For example, plants can be selected on the basis that those plants produce relatively abundant biomass or seed, produce biomass or seed that incorporate relatively high levels of specific desired components, and the like.

The *Nicotiana* species of plant can be grown under agronomic conditions so as to promote development of biomass or one or more anatomical parts. Tobacco plants can be grown in greenhouses, growth chambers, or outdoors in fields, or grown hydroponically.

According to a method such as is described in various embodiments herein, biomass or one or more anatomical parts are harvested from the *Nicotiana* species of plant. The manner by which biomass or one or more anatomical parts are harvested can vary. Typically, essentially all the biomass or anatomical parts can be harvested, and employed as such.

The time of harvest during the life cycle of the plant can vary. For example, biomass or one or more anatomical parts can be harvested when immature. Alternatively, biomass or one or more anatomical parts can be harvested after the point that the plant has reached maturity.

The post-harvest processing of biomass or one or more anatomical parts can vary. After harvest, the biomass or one or more anatomical parts, or portion thereof, can be used in the harvested form (e.g., the biomass can be used without being subjected to any curing and/or aging process steps). For example, biomass or one or more anatomical parts can be used without being subjected to significant storage, handling or processing conditions. In certain situations, it is preferable that the fresh biomass or one or more anatomical parts be used virtually immediately after harvest. Alternatively, for example, biomass or one or more anatomical parts can be refrigerated or frozen for later use, freeze dried, subjected to irradiation, yellowed, dried, cured, or otherwise subjected to storage or treatment for later use.

Harvested biomass can be physically processed. Biomass or one or more anatomical parts, or one or more parts thereof, can be further subdivided into parts or pieces (e.g., biomass can be comminuted, pulverized, milled or ground into pieces or parts that can be characterized as granules, particulates or fine powders). Biomass or one or more anatomical parts, or one or more parts thereof, can be subjected to external forces or pressure (e.g., by being pressed or subjected to roll treatment). When carrying out such processing conditions, biomass or one or more anatomical parts can have a moisture content that approximates its natural moisture content (e.g., its moisture content immediately upon harvest), a moisture content achieved by adding moisture to the biomass or a moisture content that results from the drying of the biomass. For example, powdered, pulverized, ground or milled pieces of biomass or one or more anatomical parts can have moisture contents of less than about 25 weight percent, often less than about 20 weight percent, and frequently less than about 15 weight percent. Parts or pieces of biomass or one or more anatomical parts can be used as components of tobacco products without further processing, or alternatively the particulate biomass or anatomical part material can be processed further prior to incorporation into a tobacco product.

Harvested biomass or one or more anatomical parts, or components thereof, can be subjected to other types of processing conditions. For example, components of biomass or one or more anatomical parts can be separated from one another, or otherwise fractionated into chemical classes or mixtures of individual compounds. As used herein, an "isolated biomass component," "isolated component of one or more anatomical parts," "biomass isolate," or "isolate of one or more anatomical parts" is a compound or complex mixture of compounds separated from biomass or one or more anatomical parts of a plant of the *Nicotiana* species. The isolated biomass component or isolated component of one or more anatomical parts can be a single compound, a homologous mixture of similar compounds (e.g., isomers of a flavorful or aromatic compound), or a heterologous mixture of dissimilar compounds (e.g., a complex mixture of various compounds of different types, preferably having desirable sensory attributes).

Examples of the types of components that can be present in a biomass isolate or an isolate of one or more anatomical parts include various fatty acids and various triglycerides. Exemplary fatty acids include palmitic acid, linoleic acid, oleic acid, caprylic acid, myristic acid, pentadecanoic acid, palmetoleic acid, heptadecanoic acid, heptadecenoic acid, elaidic acid, gamma-lenolenic acid, arachidic acid, arachidonic acid, 11-eicosenoic acid, 8,11,14-eicosatrieonic acid, 11, 14,17-eicosatrienoic acid, 5,8,11,14,17-eicosopentanoic acid, heniecosenoic acid, lignoceric acid, 4,7,10,15,19-decosahexanoic acid, and stearic acid. Exemplary triglycerides include trilinolein, palmito-di-linolein, di-palmito-linolein, tripalmitin, tristearin, and triolein. Exemplary components of a biomass isolate or an isolate of one or more anatomical parts also include a variety of other compounds having flavor and aroma characteristics such as amino acids and various polyphenols.

Typical separation processes can include one or more process steps such as solvent extraction (e.g., using polar solvents, non-polar organic solvents, or supercritical fluids), chromatography, distillation, filtration, cold pressing or other pressure-based techniques, recrystallization, and/or solvent-solvent partitioning. Exemplary extraction and separation solvents or carriers include water, alcohols (e.g., methanol or ethanol), hydrocarbons (e.g., heptane and hexane), diethyl ether methylene chloride and supercritical carbon dioxide. Exemplary techniques useful for extracting components from *Nicotiana* species are described in U.S. Pat. No. 4,144,895 to Fiore; U.S. Pat. No. 4,150,677 to Osborne, Jr. et al.; U.S. Pat. No. 4,267,847 to Reid; U.S. Pat. No. 4,289,147 to Wildman et al.; U.S. Pat. No. 4,351,346 to Brummer et al.; U.S. Pat. No. 4,359,059 to Brummer et al.; U.S. Pat. No. 4,506,682 to Muller; U.S. Pat. No. 4,589,428 to Keritsis; U.S. Pat. No. 4,605,016 to Soga et al.; U.S. Pat. No. 4,716,911 to Poulose et al.; U.S. Pat. No. 4,727,889 to Niven, Jr. et al.; U.S. Pat. No. 4,887,618 to Bernasek et al.; U.S. Pat. No. 4,941,484 to Clapp et al.; U.S. Pat. No. 4,967,771 to Fagg et al.; U.S. Pat. No. 4,986,286 to Roberts et al.; U.S. Pat. No. 5,005,593 to Fagg et al.; U.S. Pat. No. 5,018,540 to Grubbs et al.; U.S. Pat. No. 5,060,669 to White et al.; U.S. Pat. No. 5,065,775 to Fagg; U.S. Pat. No. 5,074,319 to White et al.; U.S. Pat. No. 5,099,862 to White et al.; U.S. Pat. No. 5,121,757 to White et al.; U.S. Pat. No. 5,131,414 to Fagg; U.S. Pat. No. 5,131,415 to Munoz et al.; U.S. Pat. No. 5,148,819 to Fagg; U.S. Pat. No. 5,197,494 to Kramer; U.S. Pat. No. 5,230,354 to Smith et al.; U.S. Pat. No. 5,234,008 to Fagg; U.S. Pat. No. 5,243,999 to Smith; U.S. Pat. No. 5,301,694 to Raymond et al.; U.S. Pat. No. 5,318,050 to Gonzalez-Parra et al.; U.S. Pat. No. 5,343,879 to Teague; U.S. Pat. No. 5,360,022 to Newton; U.S. Pat. No. 5,435,325 to Clapp et al.; U.S. Pat. No. 5,445,169 to Brinkley et al.; U.S. Pat. No. 6,131,584 to Lauterbach; U.S. Pat. No. 6,298,859 to Kierulff et al.; U.S. Pat. No. 6,772,767 to Mua et al.; and U.S. Pat. No. 7,337,782 to Thompson, each of which is incorporated herein by reference. See also, the types of separation techniques set forth in Brandt et al., LC-GC Europe, p. 2-5 (March, 2002) and Wellings, *A Practical Handbook of Preparative HPLC* (2006), which are incorporated herein by reference. In addition, the biomass or components thereof can be subjected to the types of treatments set forth in Ishikawa et al., *Chem. Pharm. Bull.*, 50, 501-507 (2002); Tienpont et al., *Anal. Bioanal. Chem.*, 373, 46-55 (2002); Ochiai, *Gerstel Solutions Worldwide*, 6, 17-19 (2006); Coleman, III, et al., *J. Sci. Food and Agric.*, 84, 1223-1228 (2004); Coleman, III et al.,*J. Sci. Food and Agric.*, 85, 2645-2654 (2005); Pawliszyn, ed., *Applications of Solid Phase Microextraction, RSC Chromatography Monographs*, (Royal Society of Chemistry, UK) (1999); Sahraoui et al., *J. Chrom.*, 1210, 229-233 (2008); and U.S. Pat. No. 5,301,694 to Raymond et al., each of which is incorporated herein by reference. See also, for example, the types of processing techniques set forth in Frega et al., *JAOCS*, 68, 29-33 (1991); Patel et al., *Tob. Res.*, 24, 44-49 (1998); Giannelos et al., *Ind. Crops Prod.*, 16, 1-9 (2002); Mukhtar et al., *Chinese J. Chem.*, 25, 705-708 (2007); and Stanisavljevic et al., *Eur. J. Lipid Sci. Technol.*, 111, 513-518 (2009), each of which is incorporated herein by reference.

Other methods of forming a biomass isolate or an isolate of one or more anatomical parts from tobacco can be employed. For example, such a method can produce a lipid-containing isolate from a tobacco biomass or anatomical part source. Methods of extracting oil components from plant biomass or one or more anatomical parts are described, for example, in U.S. Pat. No. 4,008,210 to Steele et al.; U.S. Pat. No. 4,009,290 to Okumori et al.; U.S. Pat. No. 4,045,879 to Witte; U.S. Pat. No. 4,122,104 to Witte; U.S. Pat. No. 4,298,540 to Youn et al.; U.S. Pat. No. 4,359,417 to Karnofsky et al.; U.S. Pat. No. 4,456,556 to Grimsby; U.S. Pat. No. 4,456,557 to Grimsby; U.S. Pat. No. 4,466,923 to Friedrich; U.S. Pat. No. 4,515,726 to Sullivan; U.S. Pat. No. 4,847,106 to Pike et al.; U.S. Pat. No. 5,077,071 to Strop; U.S. Pat. No. 5,296,621 to Roos et al.; U.S. Pat. No. 5,397,571 to Roland et al.; U.S. Pat. No. 5,932,095 to Walters et al.; U.S. Pat. No. 6,083,729 to Martin et al.; U.S. Pat. No. 6,225,483 to Franke; U.S. Pat. No. 6,403,126 to Webster et al.; U.S. Pat. No. 6,414,172 to Garces et al.; U.S. Pat. No. 6,417,157 to Wadsworth et al.; U.S. Pat. No. 6,495,175 to Rao et al.; U.S. Pat. No. 6,504,085 to Howard; U.S. Pat. No. 6,800,318 to Kapila et al.; U.S. Pat. No. 6,860,998 to Wilde; U.S. Pat. No. 7,074,449 to Holley et al.; U.S. Pat. No. 7,156,981 to Wilde et al.; U.S. Pat. No. 7,198,808 to Krasutsky et al.; U.S. Pat. No. 7,615,657 to Bathurst et al.; and U.S. Pat. No. 7,741,500 to Arhancet et al.; and US Patent Appl. Pub. No. 2005/0147722 to Fan et al., each of which is incorporated by reference herein.

Components of biomass or of one or more anatomical parts can be subjected to conditions so as to cause those components (whether as part of the biomass or of the one or more anatomical parts or in the form of an isolated component) to undergo chemical transformation. For example, a biomass isolate or an isolate of one or more anatomical parts that has been separated from the biomass or one or more anatomical parts can be treated to cause chemical transformation or can be admixed with other ingredients. Such chemical transformation or modification can result in changes of certain chemical and physical properties of such biomass isolate or isolate of one or more anatomical parts (e.g., sensory attributes of such an isolate). Exemplary chemical modification processes can be carried out by acid/base reaction, hydrolysis, heating, and enzymatic treatments (e.g., using hydrolyase, glycosidase, or glucosidase); and as such, components of the isolate can undergo esterification, transesterification, isomeric conversion, acetal formation, acetal decomposition, and the like. Additionally, various isolated lipid components of the biomass or one or more anatomical parts can be subjected to hydrogenation in order to alter the degree of saturation of those components, and hence alter the physical form or behavior of those components.

In one aspect, biomass or one or more anatomical parts can be cold pressed in order to squeeze lipids from the biomass or one or more anatomical parts, and those lipid components are collected and isolated; or alternatively the biomass or one or more anatomical parts can be subjected to solvent extraction using a solvent (e.g., a polar solvent or a non-polar organic solvent), and the resulting extract is collected and the extracted components are isolated. Then, any of the various biomass components or components of one or more anatomical parts may be subjected to enzymatic treatment to form an enzymatically-treated material. The enzymatically-treated material then is subjected to solvent extraction to form a biomass isolate or an isolate of one or more anatomical parts.

In one embodiment, the separating or isolating process comprises freezing harvested biomass or one or more anatomical parts or a portion thereof to form a frozen biomass or anatomical part material, processing the frozen biomass or anatomical part material into a particulate form, subjecting the particulate biomass or anatomical part material to an enzymatic treatment to chemically alter the particulate biomass or anatomical part material, and extracting the particulate biomass or anatomical part material with a solvent to produce a biomass isolate or an isolate of one or more anatomical parts. Exemplary enzymatic treatments include treatment with a glycosidase or a glucosidase.

Biomass or one or more anatomical parts and components or isolates thereof are useful as components for tobacco compositions, particularly tobacco compositions incorporated into smoking articles or smokeless tobacco products. Addition of such components according to a method such as is described in various embodiments herein to a tobacco composition can enhance a tobacco composition in a variety of ways, depending on the nature of the biomass or seed isolate and the type of tobacco composition. Exemplary such components can serve to provide flavor and/or aroma to a tobacco product (e.g., composition that alters the sensory characteristics of tobacco compositions or smoke derived therefrom). Lutein derived from biomass is suitable for use more generally in compositions that may comprise an antioxidant, an anti-inflammatory agent, an agent to prevent and/or ameliorate age-related macular degeneration, and/or an agent counteracting the deleterious effects of certain polycyclic aromatic hydrocarbons subject to activation by one or more cytochrome P450 monooxygenases.

The form of biomass isolate or isolate of one or more anatomical parts can vary. Typically, such isolate is in a solid, liquid, or semi-solid or gel form. Biomass or seed isolate can be used in concrete, absolute, or neat form. Such isolate can have a dry particulate form, a waxy form, or a thick paste form. Liquid forms include isolates contained within aqueous or organic solvent carriers.

Biomass or one or more anatomical parts, processed biomass or one or more anatomical parts, and biomass isolates or isolates from one more anatomical parts can be employed in a variety of forms. Biomass or one or more anatomical parts, or an isolate of biomass or of one more anatomical parts, can be employed as a component of processed tobaccos. In one regard, the biomass or one or more anatomical parts, or components thereof, can be employed within a top dressing formulation, or within a casing formulation for application to tobacco strip (e.g., using the types of manners and methods set forth in U.S. Pat. No. 4,819,668 to Shelar, which is incorporated herein by reference). Alternatively, the biomass or one or more anatomical parts, or components thereof, can be employed as an ingredient of a reconstituted tobacco material (e.g., using the types of tobacco reconstitution processes generally set forth in U.S. Pat. No. 5,143,097 to Sohn; U.S. Pat. No. 5,159,942 to Brinkley et al.; U.S. Pat. No. 5,598,868 to Jakob; U.S. Pat. No. 5,715,844 to Young; U.S. Pat. No. 5,724,998 to Gellatly; and U.S. Pat. No. 6,216,706 to Kumar, each of which is incorporated herein by reference). The biomass or one or more anatomical parts, or components thereof, also can be incorporated into a cigarette filter (e.g., in the filter plug, plug wrap, or tipping paper) or incorporated into cigarette wrapping paper, preferably on the inside surface, during the cigarette manufacturing process. An isolate from biomass or from one or more anatomical parts which isolate has a waxy or smooth texture can be used as a coating for the surface of a formed smokeless tobacco product. An isolate having sticky properties can be used as an adhesive (or component of an adhesive) or binding agent within tobacco products. An isolate having a oily or liquid character can be used as a solvent (e.g., to be used to replace, or act comparable to, a triglyceride type of solvent; or to replace a glycol type of solvent as a humectant or as a carrier for casing components).

Biomass or one or more anatomical parts, processed biomass or one or more anatomical parts, and biomass isolates or isolates from one more anatomical parts can be incorporated into smoking articles. The biomass or one or more anatomical parts, processed biomass or one or more anatomical parts, and biomass isolates or isolates from one more anatomical parts can be admixed with other components that are employed in the manufacture of tobacco products. Exemplary types of further ingredients that can be admixed with the biomass or anatomical part material include flavorants, fillers, binders, pH adjusters, buffering agents, colorants, disintegration aids, antioxidants, humectants and preservatives. Representative tobacco blends, non-tobacco components, and representative cigarettes manufactured therefrom, are set forth in U.S. Pat. No. 4,836,224 to Lawson et al.; U.S. Pat. No. 4,924,888 to Perfetti et al.; U.S. Pat. No. 5,056,537 to Brown et al.; U.S. Pat. No. 5,220,930 to Gentry; U.S. Pat. No. 5,360,023 to Blakley et al.; and U.S. Pat. No. 6,701,936 to Shafer et al.; and PCT WO 02/037990 to Bereman. Those tobacco materials also can be employed for the manufacture of those types of cigarettes that are described in U.S. Pat. No. 4,793,365 to Sensabaugh; U.S. Pat. No. 4,917,128 to Clearman et al.; U.S. Pat. No. 4,947,974 to Brooks et al.; U.S. Pat. No. 4,961,438 to Korte; U.S. Pat. No. 4,920,990 to Lawrence et al.; U.S. Pat. No. 5,033,483 to Clearman et al.; U.S. Pat. No. 5,074,321 to Gentry et al.; U.S. Pat. No. 5,105,835 to Drewett et al.; U.S. Pat. No. 5,178,167 to Riggs et al.; U.S. Pat. No. 5,183,062 to Clearman et al.; U.S. Pat. No. 5,211,684 to Shannon et al.; U.S. Pat. No. 5,247,949 to Deevi et al.; U.S. Pat. No. 5,551,451 to Riggs et al.; U.S. Pat. No. 5,285,798 to Banerjee et al.; U.S. Pat. No. 5,593,792 to Farrier et al.; U.S. Pat. No. 5,595,577 to Bensalem et al.; U.S. Pat. No. 5,816,263 to Counts et al.; U.S. Pat. No. 5,819,751 to Barnes et al.; U.S. Pat. No. 6,095,153 to Beven et al.; U.S. Pat. No. 6,311,694 to Nichols et al.; U.S. Pat. No. 6,367,481 to Nichols et al.; and U.S. Pat. No. 7,726,320 to Robinson et al.; and PCT WO 97/048294 to Matsuura et al. and PCT WO 98/016125 to Snaider et al. See, also, those types of commercially marketed cigarettes described *Chemical and Biological Studies on New Cigarette Prototypes that Heat Instead of Burn Tobacco*, R. J. Reynolds Tobacco Company Monograph (1988) and *Inhalation Toxicology*, 12:5, p. 1-58 (2000).

*Nicotiana* biomass or one or more anatomical parts, processed biomass or one or more anatomical parts, and biomass isolates or isolates from one more anatomical parts can be incorporated into smokeless tobacco products, such as loose moist snuff, loose dry snuff, chewing tobacco, pelletized tobacco pieces (e.g., having the shapes of pills, tablets, spheres, coins, beads, obloids or beans), extruded or formed tobacco strips, pieces, rods, cylinders or sticks, finely divided ground powders, finely divided or milled agglomerates of powdered pieces and components, flake-like pieces, molded processed tobacco pieces, pieces of tobacco-containing gum, rolls of tape-like films, readily water-dissolvable or water-dispersible films or strips (e.g., US Pat. App. Pub. No. 2006/0198873 to Chan et al.), or capsule-like materials possessing an outer shell (e.g., a pliable or hard outer shell that can be clear, colorless, translucent or highly colored in nature) and an inner region possessing tobacco or tobacco flavor (e.g., a Newtonian fluid or a thixotropic fluid incorporating tobacco of some form). Various types of smokeless tobacco products are set forth in U.S. Pat. No. 1,376,586 to Schwartz; U.S. Pat.

No. 3,696,917 to Levi; U.S. Pat. No. 4,513,756 to Pittman et al.; U.S. Pat. No. 4,528,993 to Sensabaugh, Jr. et al.; U.S. Pat. No. 4,624,269 to Story et al.; U.S. Pat. No. 4,987,907 to Townsend; U.S. Pat. No. 5,092,352 to Sprinkle, III et al.; and U.S. Pat. No. 5,387,416 to White et al.; US Pat. App. Pub. Nos. 2005/0244521 to Strickland et al. and 2008/0196730 to Engstrom et al.; PCT WO 04/095959 to Arnarp et al.; PCT WO 05/063060 to Atchley et al.; PCT WO 05/016036 to Bjorkholm; and PCT WO 05/041699 to Quinter et al., each of which is incorporated herein by reference. See also, the types of smokeless tobacco formulations, ingredients, and processing methodologies set forth in U.S. Pat. No. 6,668,839 to Williams; U.S. Pat. No. 6,834,654 to Williams; U.S. Pat. No. 6,953,040 to Atchley et al.; U.S. Pat. No. 7,032,601 to Atchley et al.; U.S. Pat. No. 7,694,686 to Atchley et al.; U.S. Pat. No. 7,861,728 to Holton, Jr. et al.; U.S. Pat. No. 7,819,124 to Strickland et al.; U.S. Pat. No. 7,810,507 to Dube et al.; and U.S. Pat. No. 8,168,855 to Nielsen et al; US Pat. Appl. Pub. Nos. 2004/0020503 to Williams, 2006/0191548 to Strickland et al.; 2007/0062549 to Holton, Jr. et al.; 2008/0029116 to Robinson et al.; 2008/0029117 to Mua et al.; and 2008/0173317 to Robinson et al., each of which is incorporated herein by reference.

Residue of biomass or anatomical part material remaining after subjecting biomass or anatomical part material to a separation process (e.g., cold pressing or solvent extraction) and removing some portion of the biomass or one or more anatomical parts can also be incorporated into a tobacco product, including any of the tobacco products mentioned herein with regard to biomass or one or more anatomical parts, or isolates therefrom. For example, a residue remaining after cold pressing biomass or one or more anatomical parts and removing lipid components can be used as a tobacco composition component (e.g., as part of a reconstituted tobacco material), and incorporated into a smoking article or a smokeless tobacco composition. The insoluble pulp residue remaining after solvent extraction of a solvent-soluble portion of a biomass or anatomical part material can likewise be used as a component of a tobacco composition.

Certain isolates, such as triglyceride-containing isolates of biomass or of one or more anatomical parts, can be used as components of capsules used in smoking articles or smokeless tobacco compositions. In particular, triglyceride-containing isolates can be combined with a flavorant and used as a diluting agent or carrier within the internal payload of certain breakable capsules. Typically, such a capsule according to a method such as is described in various embodiments herein has an outer wall and an internal liquid, solid, or gel payload. The payload is released upon rupture of the capsule wall. Exemplary capsule-containing tobacco products that could incorporate such isolates are set forth in U.S. Pat. No. 7,836,895 to Dube et al.; U.S. Pat. No. 7,861,728 to Holton et al.; U.S. Pat. No. 7,972,254 to Stokes set al.; and U.S. Pat. No. 8,066,011 to Clark et al.; and US Pat. Appl. Pub. No. 2009/0050163 to Hartmann et al., each of which is incorporated herein by reference.

Aspects of a method such as is described in various embodiments herein are more fully illustrated by an example such as may follow below, set forth to illustrate a method such as is described in various embodiments herein in certain of its various aspects and not to be construed as limiting thereof.

In connection with a method such as is described in various embodiments herein, it is found that lutein is readily derived through processing of physically and/or chemically untransformed or transformed biomass from the *Nicotiana* species.

In an embodiment, a method such as is described in various embodiments herein provides a process for isolating lutein from a quantity of tobacco biomass, the process performed at ambient temperature, the process comprising disrupting the physical integrity of the quantity of tobacco biomass, thereby forming a disrupted biomass; contacting a quantity of the disrupted biomass with an aqueous mixture, the aqueous mixture having a pH of about 8.5 and optionally comprising glycine and an alkali metal salt, thereby forming a first pigmented slurry; pressing a quantity of the first pigmented slurry, thereby forming a pressed solid and a released syrup; fractionating a quantity of the released syrup by force, thereby forming a released syrup component having a lesser sedimentation velocity and a released syrup component having a higher sedimentation velocity; contacting a quantity of an acid with a quantity of the released syrup component having a lesser sedimentation velocity, thereby forming an acidified released syrup component, said acidified released syrup component having a pH of about 5.9; contacting a quantity of the acidified released syrup component with a quantity of diatomaceous earth, thereby forming a second pigmented slurry; filtering or otherwise separating the second pigmented slurry into a predominantly solid second pigmented slurry component and a predominantly liquid second pigmented slurry component; contacting a composition comprising a quantity of at least one member of the set consisting of the released syrup component having a higher sedimentation velocity and the predominantly solid second pigmented slurry component with a composition comprising at least one solvent in which lutein is soluble, thereby forming a pigmented mixture; fractionating a quantity of the pigmented mixture, thereby forming a fraction enriched in lutein and the at least one solvent and a fraction in which lutein and the at least one solvent are less abundant; separating lutein in a quantity of the fraction enriched in lutein and the at least one solvent from the at least one solvent in the fraction enriched in lutein and the at least one solvent; thereby isolating lutein from the quantity of tobacco biomass.

According to a method such as is described in various embodiments herein, a quantity of tobacco biomass may comprise a mass of tobacco biomass anywhere in a range from a femtogram or less to a metric ton or more.

According to a method such as is described in various embodiments herein, an ambient temperature may be a temperature customarily obtained in a room, or in a laboratory, or in a field at a time concurrent with or subsequent to harvest, or in another environment. Without limitation, an ambient temperature may be a temperature between about 5 degrees Celsius and about 40 degrees Celsius. An ambient temperature may vary from one portion and/or step in a process according to a method such as is described in various embodiments herein to another.

According to a method such as is described in various embodiments herein, a disrupting of the physical integrity of a quantity of tobacco biomass can be effected via application of physical force and/or direction of electromagnetic radiation to at least a portion of the tobacco biomass and/or more generally through any means of performing work on the quantity of tobacco biomass, including, without limitation, shredding, grinding, macerating, comminuting, milling, tearing, grating, slicing, shearing, pulverizing, microwaving, lyophilizing and/or freeze-thawing.

According to a method such as is described in various embodiments herein, an aqueous mixture for contacting with a quantity of the disrupted biomass may comprise a buffer solution, in particular a buffer solution comprising glycine, and/or in particular a buffer solution comprising an alkali metal salt such as sodium chloride, sodium metabisulfite and/or sodium borate.

According to a method such as is described in various embodiments herein, a first pigmented slurry may comprise what is known in the art as "green juice."

According to a method such as is described in various embodiments herein, a pressing of the first pigmented slurry may be effected through an application of force to the first pigmented slurry by means of a screw press.

According to a method such as is described in various embodiments herein, a fractionating of a quantity of the released syrup may be effected through an application of force, and, in particular, an application of centrifugal force, such as an application of centrifugal force by means of a decanter centrifuge.

According to a method such as is described in various embodiments herein, a predominantly solid second pigmented slurry component may be retained by a suitable filter and a predominantly liquid second pigmented slurry component may traverse the suitable filter.

According to a method such as is described in various embodiments herein, an at least one solvent in which lutein is soluble may comprise an oil and/or a fat and/or a turpentine and/or a hydrocarbon and/or more generally a hydrophobic substance.

According to a method such as is described in various embodiments herein, a fractionating of a quantity of the pigmented mixture may be effected through any means known in the art suitable for such fractionation, including, without limitation, filtration and/or sedimentation.

According to a method such as is described in various embodiments herein, a separating of lutein in a quantity of the fraction enriched in lutein and the at least one solvent from the at least one solvent in the fraction enriched in lutein and the at least one solvent may be effected by filtration and/or precipitation and/or chromatographic separation and/or countercurrent flow and/or more generally any suitable process known in the art for separating a solvent from a solute. It will be noted by a person having ordinary skill in the art that conditions and/or procedures pertaining to method such as is described in various embodiments herein are notably favorable for preservation of chemical integrity and biological activity of lutein. A person having ordinary skill in the art will recognize that such conditions and/or procedures enable favorable disposition of resources, not requiring extremes of temperature or pH for operativity, and making use of material otherwise regarded as a waste stream.

A method such as is described in various embodiments herein provides a composition suitable for ingestion by a vertebrate in need and/or desirous of ingestion thereof, said product comprising lutein produced by a process according to paragraph supra and one or more suitable excipients. A need and/or desire for ingestion of such a composition may obtain when there is a need or a desire to forestall, mitigate, prevent, treat and/or ameliorate a condition to be forestalled, mitigated, prevented, treated and/or ameliorated by the ingestion of lutein, including, but not limited to, age-related macular degeneration, diminution of oxidative capacity generally, diminution of oxidative capacity in one or a plurality of various cell and/or tissue and/or organ compartments, including without limitation a vertebrate retina, or more generally any metabolic state and/or condition to be forestalled, mitigated, prevented, treated and/or ameliorated by ingestion of lutein.

A method such as is described in various embodiments herein also provides a dietary supplement and/or pharmaceutical product suitable for administration to a vertebrate in need thereof, the product comprising lutein produced by a process according to paragraph supra and one or more suitable excipients, the product disposed within a suitable container-closure system. A need for ingestion of such a composition may obtain when there is a need to forestall, mitigate, prevent, treat and/or ameliorate a condition to be forestalled, mitigated, prevented, treated and/or ameliorated by the ingestion of lutein, including, but not limited to, age-related macular degeneration, diminution of oxidative capacity generally, diminution of oxidative capacity in one or a plurality of various cell and/or tissue and/or organ compartments, including without limitation a vertebrate retina, or more generally any metabolic state and/or condition to be forestalled, mitigated, prevented, treated and/or ameliorated by ingestion of lutein.

A method such as is described in various embodiments herein additionally provides manufactured tobacco product suitable for smoking comprising lutein produced by a process according to paragraph supra.

A method such as is described in various embodiments herein further provides a smokeless tobacco product comprising lutein produced by a product according to paragraph supra.

A method such as is described in various embodiments herein also provides a process for isolating lutein from a quantity of tobacco biomass, the process performed at ambient temperature, the process comprising disrupting the physical integrity of the quantity of tobacco biomass, thereby forming a disrupted biomass; contacting a quantity of the disrupted biomass with an aqueous mixture, the aqueous mixture having a pH of about 8.5 and comprising glycine and an alkali metal salt, thereby forming a first pigmented slurry; pressing a quantity of the first pigmented slurry, thereby forming a pressed solid and a released syrup; fractionating a quantity of the released syrup by force, thereby forming a released syrup component having a lesser sedimentation velocity and a released syrup component having a higher sedimentation velocity; contacting a quantity of an acid with a quantity of the released syrup component having a lesser sedimentation velocity, thereby forming an acidified released syrup component, said acidified released syrup component having a pH of about 5.9; contacting a quantity of the acidified released syrup component with a quantity of diatomaceous earth, thereby forming a second pigmented slurry; filtering or otherwise separating the second pigmented slurry into a predominantly solid second pigmented slurry component and a predominantly liquid second pigmented slurry component; contacting a composition comprising a quantity of at least one member of the set consisting of the released syrup component having a higher sedimentation velocity and the predominantly solid second pigmented slurry component with a composition comprising at least one solvent in which lutein is soluble, thereby forming a pigmented mixture; fractionating a quantity of the pigmented mixture, thereby forming a fraction enriched in lutein and the at least one solvent and a fraction in which lutein and the at least one solvent are less abundant; separating lutein in a quantity of the fraction enriched in lutein and the at least one solvent from the at least one solvent in the fraction enriched in lutein and the at least one solvent; thereby isolating lutein from the quantity of tobacco biomass.

A method such as is described in various embodiments herein additionally provides a process according to the paragraph immediately above, wherein the ambient temperature is between about 5 degrees Celsius and about 40 degrees Celsius.

A method such as is described in various embodiments herein further provides a process for isolating lutein from a quantity of tobacco biomass, the process performed at a temperature between about 5 degrees Celsius and about 40 degrees Celsius, the process comprising disrupting the physical integrity of the quantity of tobacco biomass, thereby forming a disrupted biomass; contacting a quantity of the disrupted biomass with an aqueous mixture, the aqueous mixture having a pH of about 8.5 and comprising glycine and an alkali metal salt, thereby forming a first pigmented slurry; pressing a quantity of the first pigmented slurry with a screw press, thereby forming a pressed solid and a released syrup; fractionating a quantity of the released syrup by force, thereby forming a released syrup component having a lesser sedimentation velocity and a released syrup component having a higher sedimentation velocity; contacting a quantity of an acid with a quantity of the released syrup component having a lesser sedimentation velocity, thereby forming an acidified released syrup component, said acidified released syrup component having a pH of about 5.9; contacting a quantity of the acidified released syrup component with a quantity of diatomaceous earth, thereby forming a second pigmented slurry; filtering or otherwise separating the second pigmented slurry into a predominantly solid second pigmented slurry component and a predominantly liquid second pigmented slurry component; contacting a composition comprising a quantity of at least one member of the set consisting of the released syrup component having a higher sedimentation velocity and the predominantly solid second pigmented slurry component with a composition comprising at least one solvent in which lutein is soluble, thereby forming a pigmented mixture; fractionating a quantity of the pigmented mixture, thereby forming a fraction enriched in lutein and the at least one solvent and a fraction in which lutein and the at least one solvent are less abundant; separating lutein in a quantity of the fraction enriched in lutein and the at least one solvent from the at least one solvent in the fraction enriched in lutein and the at least one solvent; thereby isolating lutein from the quantity of tobacco biomass.

Many modifications and other embodiments of a method such as is described in various embodiments herein will come to mind to one skilled in the art to which this invention pertains having the benefit of the teachings presented in the foregoing description. Therefore, it is to be understood that a method such as is described in various embodiments herein is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed:

1. A process for isolating lutein from a quantity of tobacco biomass, the process performed at ambient temperature, the process comprising:
   (a) disrupting the physical integrity of the quantity of tobacco biomass, thereby forming a disrupted biomass;
   (b) contacting a quantity of the disrupted biomass with an aqueous mixture optionally comprising glycine, a salt of phosphoric acid, a bisulfite containing compound, a metabisulfite containing compound, a Group I or Group II halide salt, or a combination thereof, thereby forming a first pigmented slurry;
   (c) pressing a quantity of the first pigmented slurry, thereby forming a pressed solid and a released syrup;
   (d) fractionating a quantity of the released syrup by force, thereby forming a released syrup component having a lesser sedimentation velocity and a released syrup component having a higher sedimentation velocity;
   (e) contacting a quantity of an acid with a quantity of the released syrup component having a lesser sedimentation velocity, thereby forming an acidified released syrup component;
   (f) contacting a quantity of the acidified released syrup component with a quantity of diatomaceous earth, thereby forming a second pigmented slurry;
   (g) filtering or otherwise separating the second pigmented slurry into a predominantly solid second pigmented slurry component and a predominantly liquid second pigmented slurry component;
   (h) contacting a composition comprising a quantity of at least one member of the set consisting of the released syrup component having a higher sedimentation velocity and the predominantly solid second pigmented slurry component with a composition comprising at least one solvent in which lutein is soluble, thereby forming a pigmented mixture;
   (i) fractionating a quantity of the pigmented mixture, thereby forming a fraction enriched in lutein and the at least one solvent and a fraction in which lutein and the at least one solvent are less abundant;
   (j) separating lutein in a quantity of the fraction enriched in lutein and the at least one solvent from the at least one solvent in the fraction enriched in lutein and the at least one solvent;
   thereby forming an isolate containing lutein from the quantity of tobacco biomass.

2. The process according to claim 1, wherein the ambient temperature is between about 5 degrees Celsius and about 40 degrees Celsius.

3. The process according to claim 1, wherein disrupting the physical integrity of the quantity of tobacco biomass comprises shredding, grinding, macerating, comminuting, milling, tearing, grating, slicing, shearing, pulverizing, microwaving, lyophilizing and/or freeze-thawing.

4. The process according to claim 1, wherein the aqueous mixture comprises a buffer solution comprising an alkali metal salt.

5. The process according to claim 4, wherein the alkali metal salt comprises sodium chloride, sodium metabisulfite and/or sodium borate.

6. The process according to claim 1, wherein pressing the first pigmented slurry comprises an application of force to the first pigmented slurry by means of a screw press.

7. The process according to claim 1, wherein fractionating the quantity of the released syrup comprises an application of centrifugal force.

8. The process according to claim 7, wherein the application of centrifugal force is effected by means of a decanter centrifuge.

9. The process according to claim 1, wherein the predominantly solid second pigmented slurry component is retained by a suitable filter and the predominantly liquid second pigmented slurry component traverses the suitable filter.

10. The process according to claim 1, wherein the at least one solvent in which lutein is soluble comprises an oil and/or a fat and/or a turpentine and/or a hydrocarbon.

11. The process according to claim 1, wherein fractionating the quantity of the pigmented mixture comprises filtration and/or sedimentation.

12. The process according to claim 1, wherein separating of lutein in the quantity of the fraction enriched in lutein and the at least one solvent from the at least one solvent in the fraction enriched in lutein and the at least one solvent comprises filtration and/or precipitation and/or chromatographic separation and/or countercurrent flow.

13. The process according to claim 1, wherein the aqueous mixture has a pH of about 8.5.

14. The process according to claim 1, wherein the isolate containing lutein is incorporated into a tobacco product.

15. The process according to claim 14, wherein the tobacco product is a smoking article.

16. The process according to claim 14, wherein the tobacco product is a smokeless tobacco product.

* * * * *